US008119115B2

(12) United States Patent  (10) Patent No.: US 8,119,115 B2
Snyder et al.  (45) Date of Patent: Feb. 21, 2012

(54) ANTIVIRAL METHOD

(75) Inventors: Marcia Snyder, Stow, OH (US); David R. Macinga, Stow, OH (US); James W. Arbogast, Bath, OH (US)

(73) Assignee: GOJO Industries, Inc., Akron, OH (US)

( * ) Notice: Subject to any disclaimer, the term of this patent is extended or adjusted under 35 U.S.C. 154(b) by 333 days.

(21) Appl. No.: 11/499,227

(22) Filed: Aug. 7, 2006

(65) Prior Publication Data

US 2007/0184013 A1 Aug. 9, 2007

Related U.S. Application Data

(60) Provisional application No. 60/771,744, filed on Feb. 9, 2006.

(51) Int. Cl.
*A61K 31/00* (2006.01)

(52) U.S. Cl. ........................................ 424/78.3; 514/724

(58) Field of Classification Search ........................ None
See application file for complete search history.

(56) References Cited

U.S. PATENT DOCUMENTS

| | | | |
|---|---|---|---|
| 3,485,915 A | 12/1969 | Gerstein | 514/772.6 |
| 4,283,421 A | 8/1981 | Ray | 514/567 |
| 4,478,853 A | 10/1984 | Chaussee | 514/772 |
| 4,647,458 A | 3/1987 | Ueno et al. | 424/128 |
| 4,767,788 A | 8/1988 | Diana | 514/574 |
| 4,900,721 A | 2/1990 | Bansemir et al. | |
| 4,921,131 A | 5/1990 | Binderbauer | 222/52 |
| 4,956,170 A | 9/1990 | Lee | 514/772.1 |
| 5,000,867 A | 3/1991 | Heinhuis-Walther et al. | |
| 5,043,357 A * | 8/1991 | Hoffler et al. | 514/553 |
| 5,084,096 A | 1/1992 | Stovicek | |
| 5,145,663 A | 9/1992 | Simmons | 424/47 |
| 5,243,036 A | 9/1993 | Pablo Pivel Ranieri | 536/4.1 |
| 5,403,864 A | 4/1995 | Bruch | 514/721 |
| 5,441,723 A | 8/1995 | Simmons | 424/47 |
| 5,516,510 A | 5/1996 | Beilfuss | 424/65 |
| 5,632,978 A | 5/1997 | Moore | 510/159 |
| 5,770,199 A * | 6/1998 | Eibl et al. | 424/176.1 |
| 5,776,430 A | 7/1998 | Osborne | 424/43 |
| 5,885,562 A | 3/1999 | Lowry | 424/65 |
| 5,908,619 A | 6/1999 | Scholz | |
| 5,939,085 A | 8/1999 | Jacobs | 424/401 |
| 5,942,218 A | 8/1999 | Kirschner et al. | |
| 5,944,912 A | 8/1999 | Jenkins | 134/40 |
| 5,951,993 A | 9/1999 | Scholz | 424/405 |
| 6,022,551 A | 2/2000 | Jampani | 424/405 |
| 6,025,314 A | 2/2000 | Nitsch | 510/221 |
| 6,034,133 A | 3/2000 | Hendley | 514/573 |
| 6,080,417 A | 6/2000 | Kramer | 424/405 |
| 6,090,395 A | 7/2000 | Asmus | 424/401 |
| 6,107,261 A | 8/2000 | Taylor | 510/131 |
| 6,110,908 A | 8/2000 | Guthery | 514/188 |
| 6,117,436 A | 9/2000 | Flemming | 424/401 |
| 6,136,771 A | 10/2000 | Taylor | 510/388 |
| 6,183,768 B1 | 2/2001 | Harle | 424/423 |
| 6,204,230 B1 | 3/2001 | Taylor | 510/131 |
| 6,294,186 B1 | 9/2001 | Beerse et al. | |
| 6,319,958 B1 | 11/2001 | Johnson | 514/739 |
| 6,326,430 B1 | 12/2001 | Berte | 524/555 |
| 6,352,701 B1 | 3/2002 | Scholz | 424/405 |
| 6,423,329 B1 | 7/2002 | Sine et al. | |
| 6,436,885 B2 | 8/2002 | Biedermann | 510/131 |
| 6,468,508 B1 | 10/2002 | Laughlin | 424/59 |
| 6,488,943 B1 | 12/2002 | Beerse | 424/401 |
| 6,517,855 B2 | 2/2003 | Prusiner | 424/408 |
| 6,534,069 B1 | 3/2003 | Asmus | 424/401 |
| 6,569,261 B1 | 5/2003 | Aubay | 134/39 |
| 6,582,711 B1 | 6/2003 | Asmus | 424/405 |
| 6,610,314 B2 | 8/2003 | Koenig | 424/402 |
| 6,613,755 B2 | 9/2003 | Peterson | 514/63 |
| 6,623,744 B2 | 9/2003 | Asmus | 424/401 |
| 6,645,507 B2 | 11/2003 | Bettle | 424/401 |
| 6,685,952 B1 | 2/2004 | Ma | 424/401 |
| 6,719,988 B2 | 4/2004 | Prusiner | 424/405 |
| 6,720,355 B2 | 4/2004 | Prusiner | 514/557 |
| 6,723,689 B1 | 4/2004 | Hoang et al. | |
| 6,805,874 B1 | 10/2004 | Lutz | 424/401 |
| 6,838,078 B2 | 1/2005 | Wang et al. | |
| 6,894,012 B2 | 5/2005 | Sebillotte-Arnaud | 510/136 |
| 2002/0161046 A1 | 10/2002 | Konowalchuk | 514/557 |
| 2002/0165278 A1 | 11/2002 | Konowalchuk | 514/557 |
| 2002/0165279 A1 | 11/2002 | Konowalchuk | 514/557 |
| 2003/0008791 A1 * | 1/2003 | Chiang | 510/130 |
| 2003/0118619 A1 | 6/2003 | Suares | 424/401 |

(Continued)

FOREIGN PATENT DOCUMENTS

CA 2222498 10/1997

(Continued)

OTHER PUBLICATIONS

Kramer et al., Journal of Hospital Infection, Jan 2006, vol. 62, p. 98-106.*
Piret et al., Current Drug Targets, 2002, vol. 3, p. 17-30.*
Kampf et al., Clinical Microbiology Reviews, 2004, vol. 17, No. 4, p. 863-893.*
Satter et al., Infect Control Hosp Epidemiol, 2000, vol. 21, p. 516-519.*
Sickbert-Bennett et al., Am J Infect Control, 2004, vol. 32, p. 69-83.*
Sofer et al., BioPharm International, 2003, Supplement S-37-S-42.*
Dick, Elliot C. et al., "Interruption of Transmission of Rhinovirus Colds Among Human Volunteers Using Virucidal Paper Handkerchiefs," Feb. 1986, J. of Infectious Diseases, vol. 158, No. 2, pp. 352-356.

(Continued)

*Primary Examiner* — Kade Ariani

(74) *Attorney, Agent, or Firm* — Renner, Kenner, Greive, Bobak, Taylor & Weber

(57) ABSTRACT

This invention provides a method of inactivating non-enveloped virus particles. The method includes the step of contacting the virus with a virucidally-enhanced alcoholic composition that includes an alcohol, and an enhancer selected from the group consisting of cationic oligomers and polymers, proton donors, chaotropic agents, and mixtures thereof.

54 Claims, No Drawings

U.S. PATENT DOCUMENTS

| | | | |
|---|---|---|---|
| 2003/0215418 A1 | 11/2003 | Asmus | 424/78.35 |
| 2004/0001797 A1 | 1/2004 | Saud | 424/70.16 |
| 2004/0063591 A1* | 4/2004 | Borazjani et al. | 510/112 |
| 2004/0127559 A1 | 7/2004 | Prusiner | 514/517 |
| 2005/0025833 A1 | 2/2005 | Aschkenasy | 424/484 |
| 2005/0058673 A1 | 3/2005 | Scholz | 424/401 |
| 2005/0089539 A1 | 4/2005 | Scholz | 424/401 |
| 2005/0119221 A1 | 6/2005 | Xia et al. | |
| 2005/0238602 A1 | 10/2005 | Modak | 424/70.11 |
| 2006/0008494 A1 | 1/2006 | Prusiner | 424/405 |
| 2006/0051384 A1 | 3/2006 | Scholz et al. | |
| 2006/0052452 A1 | 3/2006 | Scholz | |
| 2006/0204466 A1 | 9/2006 | Littau et al. | |
| 2006/0204467 A1 | 9/2006 | Littau et al. | |
| 2006/0205619 A1 | 9/2006 | Mayhall et al. | |
| 2007/0148101 A1 | 6/2007 | Snyder et al. | |
| 2007/0184016 A1 | 8/2007 | Macinga et al. | |
| 2007/0185216 A1 | 8/2007 | Snyder et al. | |

FOREIGN PATENT DOCUMENTS

| | | |
|---|---|---|
| DE | 4221743 A1 | 1/1994 |
| EP | 0222579 A2 | 5/1987 |
| EP | 491643 | 6/1992 |
| EP | 604848 | 7/1994 |
| EP | 963158 | 12/1999 |
| EP | 707794 | 4/2001 |
| EP | 1125497 A2 | 8/2001 |
| EP | 1125498 | 8/2001 |
| GB | 1126953 | 9/1968 |
| GB | 2087724 A | 6/1982 |
| GB | 2187097 A | 9/1987 |
| GB | 2391810 | 2/2004 |
| WO | 98/30095 | 7/1998 |
| WO | 01/28340 | 4/2001 |
| WO | WO 01/28339 | 4/2001 |
| WO | WO 03/034994 A2 | 5/2003 |
| WO | 2004/101726 | 11/2004 |
| WO | WO 2005/067878 A1 | 7/2005 |
| WO | 2005/105070 | 11/2005 |
| WO | WO 2005/110090 A | 11/2005 |
| WO | WO 2006/002349 A1 | 1/2006 |
| WO | WO 2006/029255 A2 | 3/2006 |
| WO | 2006/062835 | 6/2006 |
| WO | 2006/062845 | 6/2006 |
| WO | 2006/062846 | 6/2006 |
| WO | 2006/062847 | 6/2006 |
| WO | 2006/062857 | 6/2006 |
| WO | 2006/062897 | 6/2006 |
| WO | WO 2006/099358 A2 | 9/2006 |
| WO | WO 2007/016067 A2 | 2/2007 |
| WO | WO 2007/024973 A1 | 3/2007 |
| WO | WO 2008/049454 | 2/2008 |
| WO | WO/2008/049454 | 5/2008 |

OTHER PUBLICATIONS

Turner, Ronald B. et al., "Virucidal Hand Treatments for Prevention of Rhinovirus Infection," Sep. 13, 2005, J. of Antimicrobial Chemotherapy.

Turner, Ronald B. et al., "Efficacy of Organic Acids in Hand Cleaners for Prevention of Rhinovirus Infections," Jul. 2004, Antimicrobial Agents and Chemotherapy, vol. 48, No. 7, pp. 2595-2598.

Turner, Ronald B., "New Considerations in the Treatment and Prevention of Rhinovirus Infections," Jan. 2005, Pediatric Annals, 34:1, pp. 53-60.

Turner, Ronald B., "The Treatment of Rhinovirus Infections: Progress and Potential," 2001, Antiviral Research, 49 (2001), pp. 1-14.

International Search Report for PCT/US2007/003148.

* cited by examiner

ANTIVIRAL METHOD

This application claims priority from U.S. Provisional Patent Application Ser. No. 60/771,744, filed on Feb. 9, 2006, which is hereby incorporated by reference.

TECHNICAL FIELD

The present invention relates to a method for inactivating non-enveloped viruses. The invention provides a method for producing a topical virucidal effect on mammalian skin against non-enveloped virus. A method for enhancing the efficacy of alcohol against non-enveloped viruses is also provided.

BACKGROUND OF THE INVENTION

Skin disinfectants containing one or more lower alcohols are widely known. Disinfectants containing at least about 50 weight percent alcohol exhibit antibacterial efficacy, however the antiviral efficacy of these alcohol disinfectants depends upon the type of virus.

Pathogenic viruses can be classified into two general types with respect to the viral structure: enveloped viruses and non-enveloped viruses. Some well known enveloped viruses include herpes virus, influenza virus; paramyxovirus, respiratory syncytial virus, corona virus, HIV, hepatitis B virus, hepatitis C virus, SARS-CoV, and toga virus. Non-enveloped viruses, sometimes referred to as "naked" viruses, include the families Picornaviridae, Reoviridae, Caliciviridae, Adenoviridae and Parvoviridae. Members of these families include rhinovirus, poliovirus, adenovirus, hepatitis A virus, norovirus, papillomavirus, and rotavirus.

It is known in the art that "enveloped" viruses are relatively sensitive and, thus, can be inactivated by commonly used disinfectants. In contrast, non-enveloped viruses are substantially more resistant to conventional disinfectants and are more environmentally stable than enveloped viruses. Although a number of non-enveloped viruses can be inactivated with relatively high concentrations of formaldehyde, the use of formaldehyde is undesirable because of its toxicity.

The antiviral efficacy of acid-containing disinfectants, and of disinfectants having an acidic pH, depends upon the type of virus. A few non-enveloped viruses, namely rhinovirus, feline calicivirus, and canine calicivirus, are believed to be at least somewhat affected by acid. See *Virus Taxonomy: VIIIth Report of the International Committee On Taxonomy of Viruses*, Elsevier Science & Technology Books, ISBN 0122499514, 2005, which is hereby incorporated by reference in its entirety. At least one reference suggests that a pH of less than 5 will provide efficacy against rhinovirus, and other acid labile viruses.

However, many non-enveloped viruses are known to be stable at an acid pH. These include Hepatitis A, Poliovirus, Coxsackievirus, Echovirus, Enterovirus, Adenovirus, Rotavirus, Parvovirus, Papillomavirus, and Norovirus. Thus, while acid-containing disinfectants have been reported to have some antiviral efficacy against, for example, rhinovirus, they have insufficient efficacy against other non-enveloped viruses. That is, the efficacy of these acidic disinfectants is narrow and limited.

U.S. Pat. No. 6,080,417 teaches a hand disinfectant that contains from 50 to 60 volume percent lower alcohol, a $C_{3-5}$ diol, and a synergist selected from hydrogen peroxide, alkane sulfonates, and salts of thiocyanic acid.

U.S. Pat. No. 6,034,133 teaches a hand lotion containing a $C_{1-6}$ alcohol, malic acid, and citric acid that, when applied frequently, is asserted to prevent hand-to-hand transmission of rhinoviruses. The lotion was applied to finger pads and dried. A viral suspension was applied to the same finger pads and allowed to dry for ten to fifteen minutes. The finger pads were rinsed, and a viral titration determined that the rhinovirus had been eradicated.

U.S. Pat. No. 5,043,357 teaches virucidal composition containing at least 70 weight percent ethanol and/or propanol, and from 1-5 weight percent of a short-chain organic acid. The virucidal composition is stated to have broad spectrum antiviral efficacy after periods of treatment of at least 1 to 2 minutes. The skin to be disinfected must first be treated to remove skin fats before the antiviral composition is applied.

U.S. Pub. App. No. 2002/0165278 A1 teaches a method for inactivating viruses comprising contacting the virus with a virucidally effective amount of a composition consisting essentially of a dilute aqueous solution of from 0.2 to 13 volume percent $C_{1-3}$ monohydroxy alcohol or a $C_{2-4}$ diol, and a sufficient amount of acid to adjust the pH to below 4.6. At these relatively low levels of alcohol, this composition would not be expected to have rapid antibacterial efficacy.

U.S. Pub. App. No. 2005/105070 A1 teaches an aqueous antimicrobial composition stated to have antiviral efficacy against rhinovirus, rotavirus, coronovirus, and respiratory syncytial virus. The composition includes up to 70% of an organic acid and up to 40% of a specific short-chain anionic surfactant having at least one of a large hydrophilic head group, a branched alkyl chain, or an unsaturated alkyl chain. The composition was tested for antiviral efficacy for periods of from 1 to 10 minutes. These relatively high levels of acid and anionic surfactant would be expected to be irritating to the skin, and would not be suitable for leave-on type antiviral products.

U.S. Pub. App. No. 2004/101726 A1 teaches a composition comprising from 10 to 30 volume % alcohol, from 10 to 30 volume % of a long-chain alkyl polyamine, and a halogen, such as iodine. The composition is stated to have antiviral efficacy, and was tested against poliovirus for periods of from 5 to 60 minutes. No testing of other non-enveloped viruses was reported. Also, there was no indication of contact periods of less than 5 minutes.

International Pub. App. No. WO 2001/28340 teaches an antimicrobial composition stated to have antiviral efficacy, although no test data was reported. The composition comprises a dicarboxylic acid, a metal salt, and a dermatologically acceptable carrier. Suitable metal salts include those of metals of Group I, II, IA, IV, VIB, VIII, rare earth compounds, and combinations thereof.

None of the aforementioned publications teaches methods that have broad, fast efficacy against non-enveloped viruses. Each is either limited in its spectrum of antiviral activity or requires long contact times. Therefore, it would be desirable to have a method that achieves a high level of inactivation of non-enveloped virus particles in a short amount of time. A need continues to exist for a method for rapidly inactivating most, if not all, viruses. Furthermore, a need exists for alcoholic compositions that have bacteriocidal and virucidal efficacy and may be used topically against a broad spectrum of enveloped and non-enveloped viruses. In addition, there is a need for an antiviral composition that does not require toxic, regulated, or sensitizing components.

SUMMARY OF THE INVENTION

This invention provides a method of inactivating non-enveloped virus particles, the method comprising contacting non-enveloped virus particles with a virucidally-enhanced alcoholic composition comprising a $C_{1-6}$ alcohol, and an efficacy-enhancing amount of one or more enhancers selected from the group consisting of cationic oligomers and polymers, proton donors, chaotropic agents, and mixtures thereof, with the proviso that when the alcoholic composition comprises a proton donor, the composition further comprises a synergistic amount of a cationic oligomer or polymer.

The invention further provides a method of producing a topical virucidal effect on mammalian skin against non-enveloped virus by applying a virucidally-enhanced alcoholic composition comprising a $C_{1-6}$ alcohol, and an efficacy-enhancing amount of one or more enhancers selected from the group consisting of cationic oligomers and polymers, proton donors, chaotropic agents, and mixtures thereof, with the proviso that when the alcoholic composition comprises a proton donor, the composition further comprises a synergistic amount of a cationic oligomer or polymer.

The invention still further provides a method of enhancing the efficacy of a $C_{1-6}$ alcohol against non-enveloped virus in a topical application to a surface, the method comprising combining said $C_{1-6}$ alcohol with an efficacy-enhancing amount of an enhancer selected from the group consisting of cationic oligomers and polymers, proton donors, chaotropic agents, and mixtures thereof, to form an antiviral composition, with the proviso that where the antiviral composition comprises a proton donor, the composition further comprises a synergistic amount of a cationic oligomer or polymer.

The invention further provides a virucidally-enhanced alcoholic composition comprising a $C_{1-6}$ alcohol; and an efficacy-enhancing amount of an enhancer selected from the group consisting of cationic oligomers and polymers, proton donors, chaotropic agents, and mixtures thereof, with the proviso that where the alcoholic composition comprises a proton donor, the composition further comprises a synergistic amount of a cationic oligomer or polymer, wherein said virucidal composition exhibits an efficacy against non-enveloped viruses that is higher than the efficacy of the same composition but not comprising said enhancer.

DETAILED DESCRIPTION OF ILLUSTRATIVE EMBODIMENTS

The present invention provides a method of inactivating non-enveloped virus particles. In one embodiment, the antiviral method has rapid antiviral efficacy against non-enveloped viruses including members of the families Picornaviridae, Reoviridae, Caliciviridae, Adenoviridae and Parvoviridae. More specifically, in certain embodiments, the antiviral method has rapid antiviral efficacy against non-enveloped viruses such as rhinovirus, poliovirus, adenovirus, norovirus, papillomavirus, feline calicivirus, hepatitis A virus, parvovirus, and rotavirus. In one or more embodiments, the antiviral method has rapid antiviral efficacy against adenovirus, norovirus, papillomavirus, feline calicivirus, hepatitis A virus, parvovirus, and rotavirus. Advantageously, the antiviral method has rapid antiviral efficacy against papillomavirus, feline calicivirus, hepatitis A virus, and parvovirus.

In certain embodiments, the antiviral method of the present invention is also effective in killing gram negative and gram positive bacteria, fungi, parasites, and enveloped viruses. More specifically, in certain embodiments the antiviral method has rapid anti-bacterial efficacy against gram positive bacteria such as *Staphylococcus*, and against gram negative bacteria such as *Escherichia coli*. In these or other embodiments, the present method has rapid efficacy against fungi such as *Aspergillus*. In one or more embodiments, the present method has efficacy against enveloped viruses such as herpes and influenza.

The antiviral method includes contacting the virus with an antiviral composition. The physical form of the antiviral composition is not particularly limited, and in one or more embodiments, the composition may be presented as a liquid that is poured, pumped, sprayed, or otherwise dispensed, a gel, an aerosol, or a foam, including both aerosol and non-aerosol foams. The antiviral composition may be employed on a wide variety of surfaces or substrates, including skin, porous, and non-porous surfaces. In one or more embodiments, the antiviral composition may be presented as a wipe, i.e. a tissue or cloth that is wiped over a surface. In general, the antiviral composition includes an alcohol, and an enhancer selected from cationic oligomers or polymers, proton donors, chaotropic agents, and mixtures thereof.

Advantageously, the method of the present invention has antiviral efficacy over a wide range of temperatures, including ambient temperatures of from about 25 to about 35° C. In one embodiment, the antiviral composition is brought into contact with the virus particles, and greater than 1 log kill is achieved in less than 60 seconds, in another embodiment greater than 2 log kill is achieved, and in yet another embodiment, greater than 3 log kill is achieved in less than 60 seconds. In another embodiment, greater than 3.5 log kill is achieved in less than 60 seconds, and in yet another embodiment, greater than 4 log kill is achieved in less than 60 seconds. In one or more embodiments, the virus is completely inactivated to the limits of detection of the test method within about 60 seconds. In certain embodiments, the antiviral composition is brought into contact with the virus particles, and greater than 1 log kill is achieved in less than 30 seconds, in another embodiment greater than 2 log kill is achieved, and in yet another embodiment, greater than 3 log kill is achieved in less than 30 seconds, in another embodiment, greater than 3.5 log kill is achieved in less than 30 seconds, and in yet another embodiment, greater than 4 log kill is achieved in less than 30 seconds. In one or more embodiments, the virus is completely inactivated to the limits of detection of the test method within about 30 seconds.

The antiviral composition exhibits efficacy against MS2, a non-enveloped bacteriophage that is sometimes employed in tests to indicate efficacy against non-enveloped viruses. In one embodiment, the antiviral composition is brought into contact with the non-enveloped bacteriophage MS2, and greater than 1 log kill is achieved in less than 60 seconds, in another embodiment greater than 2 log kill is achieved, and in yet another embodiment, greater than 3 log kill is achieved in less than 60 seconds. In another embodiment, greater than 3.5 log kill of MS2 virus is achieved in less than 60 seconds. In yet another embodiment, greater than 4 log kill of MS2 is achieved in less than 60 seconds. In one or more embodiments, the virus is completely inactivated to the limits of detection of the test method within about 60 seconds. In certain embodiments, the antiviral composition is brought into contact with the virus particles, and greater than 1 log kill is achieved in less than 30 seconds, in another embodiment greater than 2 log kill is achieved, and in yet another embodiment, greater than 3 log kill of MS2 is achieved in less than 30 seconds. In another embodiment, greater than 3.5 log kill of MS2 is achieved in less than 30 seconds. In yet another embodiment, greater than 4 log kill of MS2 is achieved in less than 30 seconds. In one or more embodiments, the virus is completely inactivated to the limits of detection of the test method within about 30 seconds.

In another embodiment, the antiviral composition is brought into contact with a mammalian virus, such as adenovirus, and greater than 1 log kill is achieved in less than 60 seconds, in another embodiment greater than 2 log kill is achieved, and in yet another embodiment, greater than 3 log kill is achieved in less than 60 seconds. In another embodiment, greater than 3.5 log kill is achieved in less than 60 seconds. In yet another embodiment, greater than 4 log kill is achieved in less than 60 seconds. In one or more embodiments, the virus is completely inactivated to the limits of detection of the test method within about 60 seconds. In certain embodiments, the antiviral composition is brought into contact with the adenovirus particles, and greater than 1 log kill is achieved in less than 30 seconds, in another embodiment greater than 2 log kill is achieved, and in yet another embodiment, greater than 3 log kill is achieved in less than 30 seconds. In another embodiment, greater than 3.5 log kill is achieved in less than 30 seconds. In yet another embodiment, greater than 4 log kill is achieved in less than 30 seconds. In one or more embodiments, the virus is completely inactivated to the limits of detection of the test method within about 30 seconds.

In one embodiment, the methods of bringing the antiviral composition into contact with a virus on human skin includes applying an amount of the composition to the skin, and allowing the composition to remain in contact with the skin for a suitable amount of time. In other embodiments, the composition may be spread over the surface of the skin, rubbed in, or rinsed off, allowed to dry via evaporation, or wiped off.

Advantageously, the antiviral composition of the present invention exhibits enhanced efficacy against non-enveloped viruses, when compared to the efficacy of alcohol. Whereas $C_{1-6}$ alcohols have little efficacy against non-enveloped virus, the efficacy may be enhanced by combining the $C_{1-6}$ alcohol with an efficacy-enhancing amount of an enhancer, to form an antiviral composition. In one or more embodiments, the antiviral composition exhibits an increased efficacy against non-enveloped viruses when compared to a composition containing an equivalent amount of $C_{1-6}$ alcohol. In certain embodiments, a synergistic effect is seen. In other words, the efficacy of the antiviral composition against non-enveloped virus is greater than the sum of the efficacies of equivalent amounts of the individual components.

Therefore, the present invention provides a virucidally-enhanced alcoholic composition comprising alcohol, and an enhancer. In one embodiment, the alcohol is a lower alkanol, i.e. an alcohol containing 1 to 6 carbon atoms. Typically, these alcohols have antimicrobial properties. Examples of lower alkanols include, but are not limited to, methanol, ethanol, propanol, butanol, pentanol, hexanol, and isomers and mixtures thereof. In one embodiment, the alcohol comprises ethanol, propanol, or butanol, or isomers or mixtures thereof. In another embodiment, the alcohol comprises ethanol.

Generally, the antiviral composition comprises an amount of alcohol of at least about 50 percent by weight. In embodiments where rapid antimicrobial efficacy is not a requirement, the amount of alcohol may be reduced. In one embodiment, the antiviral composition comprises at least about 60 weight percent alcohol, in another embodiment, the antiviral composition comprises at least about 65 weight percent alcohol, in yet another embodiment, the antiviral composition comprises at least about 70 weight percent alcohol, and in still yet another embodiment, the antiviral composition comprises at least about 78 weight percent alcohol, based upon the total weight of antiviral composition. More or less alcohol may be required in certain instances, depending particularly on other ingredients and/or the amounts thereof employed in the composition. In certain embodiments, the antiviral composition comprises from about 50 weight percent to about 98 weight percent alcohol, in other embodiments, the antiviral composition comprises from about 60 weight percent to about 95 weight percent of alcohol, in yet other embodiments, the antiviral composition comprises from about 65 weight percent to about 90 weight percent of alcohol, and in still other embodiments, the antiviral composition comprises from about 70 weight percent to about 85 weight percent of alcohol, based upon the total weight of the antiviral composition.

It has been found that, in certain embodiments, a cationic oligomer or polymer enhances the antiviral efficacy of alcoholic compositions against non-enveloped viruses. Cationic oligomers or polymers include, but are not necessarily limited to, cationic polysaccharides, cationic copolymers of saccharides and synthetic cationic monomers, and synthetic cationic oligomer or polymers. Synthetic cationic oligomers or polymers include cationic polyalkylene imines, cationic ethoxy polyalkylene imines, cationic poly[N-[3-(dialkylammonio)alkyl] N'[3-(alkyleneoxyalkylene dialkylammonio)alkyl] urea dichloride], vinyl caprolactam/VP/dialkylaminoalkyl alkylate copolymers, and polyquaternium polymers.

Examples of cationic oligomers or polymers include chitosan, copolymers of isophorone diisocyanate and PEG-15 cocamine, vinyl caprolactam/VP/dimethylaminoethyl methacrylate copolymer, polyquaternium-4/hydroxypropyl starch copolymer, butylmethacrylate-(2-dimethylaminoethyl) methacrylate-methylmethacrylate-copolymer, guar hydroxypropyl trimonium chloride and dilinoleyl amidopropyl dimethylammonium chloride hydroxypropyl copolymer. Examples of polyquaterniums include those listed in Table 1, below, including the INCI name and technical name.

TABLE 1

| INCI Name Poly-quaternium-X | Technical Name |
|---|---|
| -2 | Bis(2-chloroethyl)ether, polym. w. N,N'-bis[3-(dimethylamino)propyl]urea |
| -4 | Hydroxyethylcellulose Dimethyldiallylammoinum Chloride Copolymer |
| -5 | Copolymer of acrylamide and beta-methacrylyloxyethyl trimethyl ammonium methosulfate |
| -6 | Polydimethyldiallyl Ammonium Chloride |
| -7 | Dimethyldiallyl Ammonium Chloride & Acrylamide Copolymer |
| -9 | Polydimethyaminoethyl methacrylate quaternized with Methyl Bromide |
| -10 | Hydroxyethylcellulose reacted with trimethyl ammonium substituted epoxide |
| -11 | PVP N,N-Dimethyl Aminoethyl Methacrylic Acid Copolymer Diethyl Sulfate Soln |
| -14 | Ethanaminium, N,N,N-Trimethyl-2-[(2-methyl-1-oxo-2-propenyl)oxy]-, Methyl Sulfate Homopolymer |
| -15 | Acrylamide-Dimethylaminoethyl Methacrylate Methyl Chloride Copolymer |
| -16 | 3-Methyl-1-Vinylimidazolium Chloride-1-Vinyl-2-Pyrrolidinone Chloride |
| -17 | Quat salt made from Adipic acid & diethylaminopropylamine & dichloroether |
| -18 | Quat salt prepared by the reaction of adipic acid and dimethylaminopropylamine, reacted with dichloroethyl ether |
| -19 | Quat ammonium salt prepared by the reaction of polyvinyl alcohol with 2,3-epoxypropylamine |
| -20 | Quat ammonium salt prepared by the reaction of polyvinyl octadecyl ether with 2,3-epoxypropylamine |
| -22 | Acrylic Acid-Diallyldimethylammonium Chloride (DADMAC) Polymer |
| -24 | Polyquat ammonium salt of hydroxyethyl cellulose reacted with lauryl dimethyl ammonium substituted epoxide |
| -27 | Block Copolymer of Polyquaternium-2 and 17 |

TABLE 1-continued

| INCI Name Poly-quaternium-X | Technical Name |
|---|---|
| -28 | Vinylpyrrolidone/Methacrylamidopropyltrimethyl-ammonium Chloride Copolymer |
| -29 | Propoxylated Chitosan quaternized with epichlorhydrin |
| -30 | Ethanaminium, N-Carboxymethyl)-N,N-Dimethyl-2-((2-Methyl-1-Oxo-2-Propenyl)Oxy)-, Inner Salt, Polymer with Methyl 2-Methyl-2-Propenoate |
| -31 | 2-propane nitrile reaction product w/N,N-dimethylpropanediamine, Sulfate |
| -32 | Acrylamide-Dimethylaminoethyl Methacrylate Methyl Chloride (DMAEMA) Copolymer |
| -37 | Trimethylaminoethyl Methacrylate Chloride Polymer |
| -39 | Acrylic Acid (AA), Polymer w/Acrylamide & Diallyldimethylammonium Chloride(DADMAC) |
| -42 | Polyoxyethylene (dimethyliminio)ethylene-(dimethyliminio)ethylene dichloride |
| -43 | Copolymer of Acrylamide, acrylamidopropyltrimonium chloride, amidopropylacrylamide & DMAPA Monomers |
| -44 | Polyquat ammonium salt of vinylpyrrilidone & quaternized imidazoline monomers |
| -46 | Quat ammonium salt of vinylcaprolactum, vinylpyrrolidone & methylvinylimidazolium |
| -47 | Quat ammonium chloride-acrylic acid, methyl acrylate & methacrylamidopropyltrimonium Chloride |
| -48 | Copolymer of methacryolyl ethyl betaine, 2-hydroxyethylmethacrylate & methacryloylethyl-trimethylammonium chloride |
| -51 | 3,5,8-Triox-4-Phosphaundec-10-en-1-aminium, 4-Hydroxy-N,N,N,10-Tetramethyl-9-Oxo, Inner Salt, 4-Oxide, Polymer with Butyl 2-Methyl-2-Propenoate |
| -53 | Acrylic Acid (AA)/Acrylamide/Methacrylamido-propyltrimonium Chloride (MAPTAC) Copolymer |
| -54 | Polymeric quaternary ammonium salt prepared by the reaction of aspartic acid and C6-18 alkylamine with dimethylaminopropylamine and sodium chloroacetate |
| -55 | 1-Dodecanaminium, N,N-Dimethyl-N-[3-[(2-Methyl-1-Oxo-2-Propenyl)AminoPropyl]-, Chloride, Polymer with N-[3-(Dimethylamino)Propyl]-2-Methyl-2-Propenamide and 1-Ethenyl-2-Pyrrolidinone |
| -56 | Polymeric quaternary ammonium salt prepared by the reaction of aspartic acid and C6-18 alkylamine with dimethylaminopropylamine and sodium chloroacetate. |
| -57 | Polymeric quaternary ammonium salt consisting of Castor Isostearate Succinate (q.v.) and Ricinoleamido-propyltrimonium Chloride (q.v.) monomers |
| -58 | 2-Propenoic Acid, Methyl Ester, Polymer with 2,2-Bis[(2-Propenyloxy)Methyl]-1-Butanol and Diethenylbenzene, Reaction Products with N,N-Dimethyl-1,3-Propanediamine, Chloromethane-Quaternized |
| -59 | Polyquaternium polyester |
| -60 | 9-Octadecenoic Acid, 12-Hydroxy-, [(2-Hydroxy-ethyl)Imino]Di-2,1-Ethanediyl Ester, Polymer with 5-Isocyanato-1-(Isocyanatomethyl)-1,3,3-Trimethylcyclohexane, Compd. with Diethyl Sulfate |
| -62 | Polymeric quaternary ammonium salt prepared by the reaction of butyl methacrylate, polyethylene glycol methyl ether methacrylate, ethylene glycol dimethacrylate and 2-methacryloyethyl trimonium chloride with 2,2'-azobis(2-methyl propionamidine) dihydrochloride |
| -63 | Copolymer of acrylamide, acrylic acid and aethyltrimonium chloride crylate |
| -65 | Polymeric quaternary ammonium salt consisting of 2-methacryloyloxyethylphosphorylcholine, butyl methacrylate and sodium methacrylate monomers |
| -68 | Quaternized copolymers of vinylpyrrolidone (VP), methacrylamide(MAM) vinylimidazole(VI) & quaternized vinylimidazole (QVI) |

In one or more embodiments, the polyquaternium polymer includes polyquaternium-2, polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-32, polyquaternium-37, polyquaternium-39, polyquaternium-42, polyquaternium-43, polyquaternium-44, polyquaternium-46, polyquaternium-47, polyquaternium-51, polyquaternium-53, polyquaternium-55, polyquaternium-57, polyquaternium-58, polyquaternium-59, polyquaternium-60, polyquaternium-63, polyquaternium-64, polyquaternium-65, polyquaternium-68, or mixtures thereof.

In one embodiment, the polyquaternium polymer includes polyquaternium-2, polyquaternium-4, polyquaternium-6, polyquaternium-7, polyquaternium-11, polyquaternium-16, polyquaternium-22, polyquaternium-28, polyquaternium-32, polyquaternium-37, polyquaternium-39, polyquaternium-42, polyquaternium-47, polyquaternium-51, polyquaternium-53, polyquaternium-55, polyquaternium-58, or mixtures thereof. In another embodiment, the polyquaternium polymer includes polyquaternium-37.

In certain embodiments, the cationic oligomer or polymer is characterized by a charge density that may be determined by methods known in the art, such as colloidal titration. In one embodiment, the charge density of the cationic oligomer or polymer is at least about 0.1 meq/g, in another embodiment at least about 2.5 meq/g, and in yet another embodiment, at least about 5 meq/g.

Advantageously, it has been found that antiviral compositions comprising alcohol and an efficacy-enhancing amount of cationic oligomer or polymer have increased efficacy against a broad spectrum of non-enveloped viruses, when compared to antiviral compositions comprising alcohol without cationic oligomer or polymer. In certain embodiments, cationic oligomers or polymers that exhibit no efficacy on their own against non-enveloped viruses, provide an enhanced efficacy when combined with alcohol according to the present invention.

In one embodiment, an efficacy-enhancing amount of cationic oligomer or polymer is at least about 0.02 percent by weight, based upon the total weight of the antiviral composition, in another embodiment at least about 0.05, and in yet another embodiment at least about 0.1 percent by weight, based upon the total weight of the antiviral composition. Generally, an efficacy-enhancing amount of cationic oligomer or polymer is from about 0.02 to about 20 percent by weight, based upon the total weight of the antiviral composition. In one embodiment, the cationic oligomer or polymer is present in an amount of from about 0.1 to about 10 weight percent, in another embodiment, the cationic oligomer or polymer is present in an amount of from about 0.25 to about 5 percent by weight, and in yet another embodiment, from about 0.4 to about 1 percent by weight, based upon the total weight of the antiviral composition. In certain embodiments, the amount of cationic oligomer or polymer may affect the viscosity of the antiviral composition, as well as other aesthetic qualities. Nevertheless, it will be understood that greater amounts of cationic oligomer or polymer can be employed, if desired, and are expected to perform at least equally as well, in terms of antiviral efficacy.

The cationic oligomer or polymer may be supplied in the form of a dry powder, or as an emulsion or liquid mixture. In one embodiment, the cationic oligomer or polymer is added to the antiviral composition as a solid. In another embodiment, the cationic oligomer or polymer is added to the antiviral composition as a solution or emulsion. In other words, the cationic oligomer or polymer may be premixed with a carrier, and optionally one or more other ingredients, to form a cationic oligomer or polymer solution or emulsion, with the proviso that the carrier does not deleteriously affect the antiviral properties of the composition. More specifically, a carrier deleteriously affects the antiviral properties of the composition when it decreases the log kill by more than a de minimus amount. By de minimus is meant a decrease of less than about 0.5 log kill.

Examples of carriers include water, alcohol, or blends of water and another carrier such as glycols, ketones, linear and/or cyclic hydrocarbons, triglycerides, carbonates, silicones, alkenes, esters such as acetates, benzoates, fatty esters, glyceryl esters, ethers, amides, polyethylene glycols, PEG/PPG copolymers, inorganic salt solutions such as saline, and mixtures thereof. It will be understood that, when the cationic oligomer or polymer is premixed to form a cationic oligomer or polymer solution or emulsion, the amount of solution or emulsion that is added to the antiviral composition is selected so that the amount of cationic oligomer or polymer falls within the ranges set forth hereinabove.

In certain embodiments, the antiviral composition further includes a proton donor. Proton donors include Arrhenius acids, Bronsted-Lowry acids and Lewis acids. Strong or weak acids may be used.

Examples of acids include mineral acids and organic acids. Mineral acids include, without limitation, hydrochloric acid, nitric acid, phosphoric acid, phosphonic acid, boric acid, and sulfuric acid. Organic acids include sulfonic acids, organophosphorus acids, carboxylic acids such as benzoic acids, propionic acids, phthalic acids, butyric acids, acetic acids, amino acids, and other substituted and unsubstituted organic acids.

Examples of organic acids include adipic acid, benzene 1,3,5 tricarboxylic acid, chlorosuccinic acid, choline chloride, cis-aconitic acid, citramalic acid, citric acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, lactic acid, maleic acid, malic acid, malonic acid, nitrilotriacetic acid, oxalacetic acid, oxalic acid, phytic acid, p-toluenesulfonic acid, salicylic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxo-glutaric acid, dl-glyceric acid, and 2,5 furandicarboxylic acid.

In certain embodiments, the proton donor includes a hydroxy carboxylic acid, and in one embodiment, the hydroxy acid includes two or more carboxylic acid groups. In one or more embodiments, the hydroxy carboxylic acid includes alpha-hydroxy acids and beta-hydroxy acids. Examples of alpha-hydroxy acids having two or more carboxylic acid groups include tartaric acid, malic acid, citric acid, and isocitric acid. Examples of other alpha-hydroxy carboxylic acids include lactic acid, tartronic acid, and malonic acid. In one embodiment, the proton donor includes citric acid, lactic acid, malic acid, tartaric acid, salicylic acid, oxalic acid, or mixtures thereof. In one embodiment, the proton donor includes citric acid.

It has been found that, in certain embodiments, a proton donor enhances the antiviral efficacy of alcoholic solutions against non-enveloped viruses. In one or more embodiments, proton donors that exhibit moderate or no efficacy on their own against non-enveloped viruses, provide an enhanced efficacy when present in the antiviral composition of the present invention.

In one or more embodiments, a synergistic enhancement of antiviral efficacy may be achieved by contacting non-enveloped virus particles with a virucidally-enhanced alcoholic composition comprising a $C_{1-6}$ alcohol, an efficacy-enhancing amount of a proton donor, and a synergistic amount of a cationic oligomer or polymer. The minimum amount of cationic oligomer or polymer that corresponds to a synergistic amount is at least about 0.02 percent by weight, based upon the total weight of the antiviral composition, in another embodiment at least about 0.05, and in yet another embodiment at least about 0.1 percent by weight, based upon the total weight of the antiviral composition.

The amount of proton donor is not particularly limited, so long as it is at least an efficacy-enhancing amount. The minimum amount of proton donor that corresponds to an efficacy-enhancing amount can be determined by comparing the log kill of virus achieved by a composition comprising an alcohol to a composition comprising an alcohol and a given amount of proton donor. The amount of proton donor below which no difference in log kill is 10 seen is an efficacy-enhancing amount. In certain embodiments, for example when efficacy against MS2 virus is desired, the minimum efficacy-enhancing amount of proton donor is about 0.01 percent by weight, based upon the total weight of the antiviral composition. In another embodiment, for example when efficacy against feline calicivirus is desired, the minimum efficacy-enhancing amount of proton donor is about 0.04 percent by weight, based upon the total weight of the antiviral composition.

In one embodiment, the proton donor is added in an amount of from about 0.01 to about 1 weight percent, based upon the total weight of the antiviral composition. In another embodiment, the amount of proton donor is from about 0.015 to about 0.5 weight percent, and in yet another embodiment, from about 0.03 to about 0.3 weight percent, based upon the total weight of the antiviral composition. It will be understood that greater levels of proton donor can be used, if desired, and are expected to perform at least equally as well.

In one embodiment, the proton donor is added to the antiviral composition as a solution or emulsion. In other words, the proton donor may be premixed with a carrier, and optionally one or more other ingredients, to form a proton donor solution or emulsion, with the proviso that the carrier does not deleteriously affect the antiviral properties of the composition. Examples of carriers include water, alcohol, any of the blends described above as carriers for the cationic oligomer or polymer, and mixtures thereof. It will be understood that, when the proton donor is premixed to form a proton donor solution or emulsion, the amount of solution or emulsion that is added to the antiviral composition is selected so that the amount of proton donor falls within the ranges set forth hereinabove.

In certain embodiments, the antiviral composition includes a chaotropic agent. Chaotropic agents include agents that disrupt molecular structure, particularly molecular structure formed by nonbonding forces such as hydrogen bonding, Van der Waals interaction, and hydrophobic effect. Chaotropic agents are well known in the field of biochemistry and include, but are not limited to, urea, thiourea, guanidine-HCl, guanidine thiocyanate, aminoguanidine bicarbonate, guanidine carbonate, guanidine phosphate, and aminoguanidine-HCL. Although is it known in the art that heat may act as a chaotropic agent, for purposes of this specification, the term chaotropic agent refers to a substance other than heat. This should not be interpreted to exclude the presence of heat from the method of the present invention, because as stated hereinbelow, the method of the present invention operates over a wide range of temperatures.

In one embodiment, the chaotropic agent comprises urea. The chaotropic agent may be supplied in the form of a dry powder, or as an emulsion or liquid mixture, and can optionally include a carrier such as those described above for the cationic oligomer or polymer.

It has been found that, in certain embodiments, the presence of a chaotropic agent enhances the antiviral efficacy of alcoholic solutions against non-enveloped viruses. Advantageously, a synergistic antiviral effect is observed when the chaotropic agent is combined with alcohol and a cationic oligomer or polymer. Without wishing to be bound by theory, it is believed that the chaotropic agent may enhance the antiviral efficacy of the alcoholic composition by disrupting the proteins of the virus capsid. In certain embodiments, chaotropic agents that exhibit no efficacy on their own against non-enveloped viruses, provide an enhanced efficacy when combined with alcohol according to the present invention. In contrast to views expressed in the prior art, where concentrations of about 6-8 M are advocated for chaotropic agents in order to denature proteins, it has surprisingly been found that the antiviral method of the present invention provides good antiviral efficacy at much lower concentrations of chaotrope.

The amount of chaotropic agent is not particularly limited, so long as it is at least an efficacy-enhancing amount. The minimum amount of chaotropic agent that corresponds to an efficacy-enhancing amount can be determined by comparing the log kill of virus achieved by a composition comprising an alcohol to a composition comprising an alcohol and a given amount of chaotropic agent. The amount of chaotropic agent below which no difference in log kill is seen is an efficacy-enhancing amount.

In one embodiment, the chaotropic agent is added in an amount of from about 0.25 to about 20 weight percent, based upon the total weight of the antiviral composition. In another embodiment, the amount of chaotropic agent is from about 1 to about 15 weight percent, and in yet another embodiment, from about 4 to about 12 weight percent, based upon the total weight of the antiviral composition. It will be understood that greater levels of chaotropic agent can be used, if desired, and are expected to perform equally as well.

As described hereinabove, the antiviral composition of this invention includes an alcohol, and an enhancer selected from cationic oligomers or polymers, proton donors and chaotropic agents. The composition can further comprise a wide range of optional ingredients, with the proviso that they do not deleteriously affect the antiviral efficacy of the composition. By deleterious is meant that the decrease in the log kill is not de minimus, or in other words, the log kill does not decrease by more than about 0.5. The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Nonlimiting examples of functional classes of ingredients are described at page 537 of the Handbook. Examples of these functional classes include: abrasives, anti-acne agents, anticaking agents, antioxidants, binders, biological additives, bulking agents, chelating agents, chemical additives; colorants, cosmetic astringents, cosmetic biocides, denaturants, drug astringents, emulsifiers, external analgesics, film formers, fragrance components, humectants, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, and keratolytics, topical active ingredients, and the like. In one embodiment, the antiviral composition further comprises glycerin.

Foaming surfactants may be included, with the proviso that they will not deleteriously affect the antiviral efficacy of the composition. The foaming surfactant contributes foaming properties to the alcoholic composition, and may include anionic, cationic, nonionic, zwitterionic, or amphoteric surfactants and their associated salts. In one embodiment, the foaming surfactant includes a fluorosurfactant, a siloxane polymer surfactant, or a combination thereof. Fluorosurfactants include compounds that contain at least one fluorine atom. Examples of fluorosurfactants include perfluoroalkylethyl phosphates, perfluoroalkylethyl betaines, fluoroaliphatic amine oxides, fluoroaliphatic sodium sulfosuccinates, fluoroaliphatic stearate esters, fluoroaliphatic phosphate esters, fluoroaliphatic quaternaries, fluoroaliphatic polyoxyethylenes, and the like, and mixtures thereof.

Examples of fluorosurfactants include perfluoroalkylethyl phosphates, perfluoroalkylethyl betaines, fluoroaliphatic amine oxides, fluoroaliphatic sodium sulfosuccinates, fluoroaliphatic phosphate esters, and fluoroaliphatic quaternaries. Specific examples of fluorosurfactants include DEA-C8-18 perfluoroalkylethyl phosphate, TEA-C8-18 perfluoroalkylethyl phosphate, $NH_4$—C8-18 perfluoroalkylethyl phosphate, and C8-18 perfluoroalkylethyl betaine.

Siloxane polymer surfactants may be generally characterized by containing one or more Si—O—Si linkages in the polymer backbone. The siloxane polymer surfactant may or may not include a fluorine atom. Therefore, some foaming surfactants may be classified as both fluorosurfactants and siloxane polymer surfactants. Siloxane polymer surfactants include organopolysiloxane dimethicone polyols, silicone carbinol fluids, silicone polyethers, alkylmethyl siloxanes, amodimethicones, trisiloxane ethoxylates, dimethiconols, quaternized silicone surfactants, polysilicones, silicone crosspolymers, and silicone waxes.

Examples of siloxane polymer surfactants include dimethicone PEG-7 undecylenate, PEG-10 dimethicone, PEG-8 dimethicone, PEG-12 dimethicone, perfluorononylethyl carboxydecal PEG 10, PEG-20/PPG-23 dimethicone, PEG-11 methyl ether dimethicone, bis-PEG/PPG-20/20 dimethicone, silicone quats, PEG-9 dimethicone, PPG-12 dimethicone, fluoro PEG-8 dimethicone, PEG 23/PPG 6 dimethicone, PEG 20/PPG 23 dimethicone, PEG 17 dimethicone, PEG5/PPG3 methicone, bis PEG20 dimethicone, PEG/PPG20/15 dimethicone copolyol and sulfosuccinate blends, PEG-8 dimethicone\dimmer acid blends, PEG-8 dimethicone\fatty acid blends, PEG-8 dimethicone\cold pressed vegetable oil\polyquaternium blends, random block polymers and mixtures thereof.

The amount of foaming surfactant is not particularly limited, so long as an effective amount to produce foaming is present. In certain embodiments, the effective amount to produce foaming may vary, depending upon the amount of alcohol and other ingredients that are present. In one or more embodiments, the alcoholic composition includes at least about 0.002 wt. % of foaming surfactant, based upon the total weight of the alcoholic composition. In another embodiment, the alcoholic composition includes at least about 0.01 wt. % of foaming surfactant, based upon the total weight of the alcoholic composition. In yet another embodiment, the alcoholic composition includes at least about 0.05 wt. % of foaming surfactant, based upon the total weight of the alcoholic composition.

Foamable alcoholic compositions are described in co-pending U.S. patent application Ser. No. 11/438,664, which is hereby incorporated by reference in its entirety.

In certain embodiments, alcohol is the only active antimicrobial or preservative ingredient introduced into the composition. Any antimicrobial or preservative ingredient other than alcohol may be referred to as an auxiliary antimicrobial agent. In one embodiment, the amount of auxiliary antimicrobial agent is less than about 0.1 percent by weight, in another embodiment, less than about 0.05 percent by weight, based upon the total weight of the antiviral composition. In another embodiment, the antiviral composition is devoid of auxiliary antimicrobial agents.

It is envisioned that, in other embodiments, auxiliary antimicrobial agents could be included, with the proviso that the antimicrobial ingredient does not deleteriously affect the antiviral properties of the composition. Examples of auxiliary antimicrobial agents include, but are not limited to, triclosan, also known as 5-chloro-2(2,4-dichlorophenoxy)phenol and available from Ciba-Geigy Corporation under the tradename IRGASAN®; chloroxylenol, also known as 4-chloro-3,5-xylenol, available from Nipa Laboratories, Inc. under the tradenames NIPACIDE® MX or PX; hexetidine, also known as 5-amino-1,3-bis(2-ethylhexyl)-5-methyl-hexahydropyrimidine; chlorhexidine salts including chlorhexidine gluconate and the salts of N,N"-Bis(4-chlorophenyl)-3,12-diimino-2,4,11,14-tetraazatetradecanediimidi amide; 2-bromo-2-nitropropane-1; 3-diol, benzalkonium chloride; cetylpyridinium chloride; alkylbenzyldimethylammonium chlorides; iodine; phenol derivatives, povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin (also known as DMDM hydantoin or glydant); phenoxyethanol; cis isomer of 1-(3-chloroallyl)-3,5,6-triaza-1-azoniaadamantane chloride, also known as quaternium-15 and available from Dow Chemical Company under the tradename DOWCIL™ 2000; diazolidinyl urea; benzethonium chloride; methylbenzethonium chloride; transition metal compounds such as silver, copper, magnesium, zinc compounds; hydrogen peroxide, chorine dioxide, and mixtures thereof. When used, the auxiliary antimicrobial agents are present in amounts of from about 0.1 to about 1 percent by weight, based upon the total weight of the antiviral composition.

In certain embodiments, the combination of alcohol and enhancer is the virucidally active ingredient, and the amount of other virucidally active materials is limited. In one embodiment, the amount of auxiliary virucidally active materials is less than about 0.1 percent by weight, in another embodiment less than about 0.05 percent by weight, and in another embodiment, less than about 0.02 percent by weight, based upon the total weight of the antiviral composition. In another embodiment, the antiviral composition is devoid of auxiliary virucidally active material It is envisioned that, in other embodiments, auxiliary antiviral agents could be included, with the proviso that the antiviral ingredient does not deleteriously affect the antiviral properties of the composition according to the present invention. Examples of auxiliary antivirals include botanicals such as rosmarinic acid, tetrahydrocurcuminoids, oleuropen, oleanolic acid, aspalathus linearis extract, white tea, red tea, green tea extract, neem oil limonoids, coleus oil, licorice extract, burnet, ginger & cinnamon extracts, alpha-glucan oligosaccharide, perilla ocymoides leaf powder, camphor, camellia oleifera leaf extract, ginger, menthol, eucalyptus, capillisil hc, hydroxyprolisilane cn, sandlewood oil/resin, calendula oil, rosemary oil, lime/orange oils, and hop acids.

Advantageously, certain ingredients that have been designated in the prior art as critical to achieving rapid antiviral efficacy can be limited in the antiviral composition of the present invention. For example, zinc compounds are not necessary, and can be limited, if desired, to less than about 0.5 percent by weight, or in another embodiment to less than about 0.1 percent by weight, based upon the total weight of the disinfecting composition. In another embodiment, the disinfecting composition is devoid of organic salts of zinc. Zinc compounds that may be so limited include those having a counterion selected from gluconate, acetate, chloride, acetylacetonate, bromide citrate, formate, glycerophosphate, iodide, lactate, nitrate, salicylate, sulfate, pyrithione, and tartrate.

In certain embodiments, the amount of metal salts in the composition is limited. In one embodiment, the amount of metal salts is less than about 0.05 percent by weight, in another embodiment, less than about 0.01 percent by weight, and in yet another embodiment, less than about 0.001 weight percent, based upon the total weight of the antiviral composition. In another embodiment, the antiviral composition is devoid of metal salts. In certain embodiments, the amount of iodine in the composition is limited. In one embodiment, the amount of iodine is less than about 1 percent by weight, in another embodiment, less than about 0.1 percent by weight, and in yet another embodiment, less than about 0.01 percent by weight, based upon the total weight of the antiviral composition. In another embodiment, the antiviral composition is devoid of iodine.

In certain embodiments, the amount of complexes of aluminum or zirconium is limited. In one embodiment, the amount of complexes of aluminum or zirconium is less than about 0.05 percent by weight, in another embodiment, less than about 0.01 percent by weight, and in yet another embodiment, less than about 0.001 weight percent, based upon the total weight of the antiviral composition.

In certain embodiments, the amount of fatty acid may be limited. In these embodiments, the amount of fatty acid may be less than about 1 percent by weight, in another embodiment less that about 0.1 percent by weight, in yet another embodiment, less than about 0.05 percent by weight, based upon the total weight of the antiviral composition. In another embodiment, the antiviral composition is devoid of fatty acid. In these or other embodiments, the amount of fatty ester may be limited. In these embodiments, the amount of fatty ester may be less than about 1 percent by weight, in another embodiment less that about 0.1 percent by weight, in yet another embodiment, less than about 0.05 percent by weight, based upon the total weight of the antiviral composition. In another embodiment, the antiviral composition is devoid of fatty ester.

Indeed, any component other than the alcohol and enhancer is not necessary to achieve antimicrobial efficacy and can optionally be limited to less than about 0.5 percent by weight, if desired to less than about 0.1 percent by weight, if desired to less than about 0.01 percent by weight, or if desired to less than about 0.001 percent by weight, based upon the total weight of the antiviral composition.

In one or more embodiments, the balance of the alcoholic composition includes water or other suitable solvent. The antiviral composition may be prepared by simply mixing the components together. In one embodiment, where the cationic oligomer or polymer is obtained as a solid powder, the antiviral composition is prepared by a method comprising dispersing the cationic oligomer or polymer in water, adding alcohol with slow to moderate agitation, and then adding other ingredients as desired, and mixing until the mixture is homogeneous.

As stated hereinabove, the antiviral composition of the present invention may be embodied in a variety of forms, including as a liquid, gel, or foam. Surprisingly, it has been found that the viscosity of the liquid antiviral composition does not affect the disinfecting efficacy of the composition. For example, in one or more embodiments of the present invention, the same amount of log kill is achieved with a liquid antiviral composition having a viscosity of 5 centipoise (cPs) and a disinfecting composition having a viscosity of about 2000 cPs. Thus it will be understood that the viscosity of the antiviral composition of the present invention is not limited.

It will also be understood that the viscosity of the antiviral composition may be affected by the relative amounts of ingredients. For example, a decrease in the relative amount of certain polyquaternium polymers may result in a lower viscosity. Also, the type of polyquaternium polymer can affect the viscosity of the antiviral composition. For example, when a non-thickening cationic oligomer or polymer, such as polyquaternium-22, is employed, the amount of cationic oligomer or polymer may not substantially affect the viscosity of the antiviral composition.

In one embodiment, where the antiviral composition is a liquid, the viscosity is from about 0 cPs to about 5000 cPs, in another embodiment, from about 50 to about 500 cPs, and in another embodiment, from about 100 to about 400 cPs, as measured by Brookfield RV Viscometer using RV and/or LV Spindles at 22° C.+/−3° C.

Surprisingly, it has been found that the antiviral composition may provide antiviral efficacy over a wide range of pH. Antiviral efficacy may be achieved at a pH of from 0 to about 14. More specifically, in one or more embodiments of the present invention, 3 log kill or greater against non-enveloped viruses is achieved with antiviral compositions having a pH of greater than about 2.5, in other embodiments greater than about 3, in yet other embodiments greater than about 3.5, in other embodiments greater than about 4, in still yet other embodiments greater than about 4.5, and in still other embodiments, greater than about 5. In certain embodiments, 3 log kill or greater against non-enveloped viruses is achieved with antiviral compositions having a pH of from about 4.5 to about 9, in other embodiments from about 5 to about 8.5, and in yet other embodiments from about 5.5 to about 7.5.

In order to demonstrate the practice of the present invention, the following examples have been prepared and tested. The examples should not, however, be viewed as limiting the scope of the invention. The claims will serve to define the invention.

EXAMPLES

[Bacteriophage Propagation]

MS2 (obtained from ATCC) was grown to high titres on *E. coli* ATCC 15597. An exponentially growing culture of *E. coli* in LB broth supplemented with 2 mM $CaCl_2$ was divided into 200 microliter aliquots and inoculated with 200 microliters of serially diluted phage stock. The mixtures were added to 2.5 ml molten soft (0.7%) MS agar held at 44° C. and immediately poured over the surface of an LB agar plate. After 16 hours incubation at 37° C., phage were harvested from plates demonstrating complete lysis of the *E. coli* lawn. To harvest the phage, 10 mL of sterile SM buffer was added to the surface of the plate and the soft agar was broken with a bent sterile glass rod. The broken agar was centrifuged for 10 minutes at 5000 G to remove debris and the supernatant containing purified phage was treated with chloroform and stored for up to 2 months at 4° C. Prior to use, phage suspensions were allowed to equilibrate to room temperature.

[Bacteriophage Titre]

Infectious particles were counted by using a soft agar overlay technique. Molten, soft (0.7%) MS agar was dispensed in 2.5 ml aliquots in glass bottles and held at 44° C. Phage-containing solutions were serially diluted in SM buffer at 20° C. and 0.1 ml added, together with 0.1 ml exponential culture of *E. coli* ATCC 15597 to the molten agar. The contents were gently mixed and poured over the surface of a nutrient agar plate. Plaques were countable after 24 hours incubation at 37° C. and results expressed as plaque forming units per milliter ($pfu\ ml^{-1}$).

[Virucidal Suspension Tests with MS2]

Suspension tests with MS2 were performed essentially as follows. Typically, 100 μl phage was added to 9.9 ml of antiviral composition. After the desired contact time at 25° C., 0.1 ml suspension was neutralized by dilution into 9.9 ml D.E. broth. Further 10-fold serial dilutions were prepared in D.E. broth. The remaining active phage was quantified by infecting *E. coli* and using the soft agar overlay method as described above.

[Virucidal Suspension Tests with Mammalian Viruses]

Virucidal suspension tests with mammalian viruses were performed using a modification of the Standard Test Method for Efficacy of Virucidal Agents Intended for Special Applications (ASTM E1052). Viral strains and indicator cells lines were as follows: Rhinovirus type 37, ATCC VR-1147 grown on MRC-5 human embryonic lung cells; Feline calicivirus Strain F-9, ATCC VR-782 grown on CRFK feline kidney cells, Adenovirus type 2, ATCC VR-846 grown on A-549 human lung carcinoma cells; Rotavirus WA, ATCC VR-2018, grown on MA-104 rhesus monkey kidney cells; Herpes Simplex Type 1 Strain F(1), ATCC VR-733 grown on rabbit kidney cells (RK) from ViroMed Laboratories; Hepatitis A Virus Strain HM-175 was grown on Fetal Rhesus monkey kidney cells (FRhK-4) from AppTec Laboratory Services; Canine Parvovirus Strain Cornell, ATCC VR-72017, was grown on A-72 canine tumor cells from ViroMed Laboratories. A 4.5 ml aliquot of each test substance was dispensed into separate sterile 15 ml conical tubes and each was mixed with a 0.5 ml aliquot of the stock virus suspension. The mixtures were vortex mixed for 10 seconds and held the remainder of the 30 second exposure time at 33±2° C. Immediately following the exposure period, a 0.1 ml aliquot was removed from each tube and the mixtures were titered by 10-fold serial dilutions and assayed for the presence of virus by infecting indicator cell lines. Cytopathic effect (CPE) was used in each case to indicate infection and TCID50 values were calculated by the method of Spearman Karber. Virus controls, neutralization controls, and cytotoxicity controls were also performed.

[Preparation and Testing of Antiviral Compositions]

Example 1

95% ethanol was mixed with water to form a 78% by weight ethanol mixture.

Example 2 was prepared as described for Example 1, except that 1.25 wt. % of 1 M citric acid in water was added, with stirring, to form a homogeneous mixture.

Example 3

Powdered Synthalen CR (polyquaternium-37) was added to water in a flask, and mixed until a smooth gel was formed. 78% ethanol was added to the flask, with stirring, to form a homogeneous mixture.

Example 4

Powdered Synthalen CR (polyquaternium-37) was added to water in a flask, and mixed until a smooth gel was formed. 78% ethanol was added to the flask, with stirring, to form a homogeneous mixture. 1.25 wt. 5 of 1 M citric acid in water was added, with mixing.

The antiviral efficacy of Examples 1-4 were tested as described above for MS2, and the results are shown in Table 2.

TABLE 2

| EXAMPLE | COMPOSITION | LOG KILL, MS2[1] |
| --- | --- | --- |
| 1 | 78% ethanol | 0.2 |
| 2 | 78% ethanol + 0.25% citric acid | 0.7 |
| 3 | 78% ethanol + 0.4% polyquaternium-37 | 0.9 |
| 4 | 78% ethanol + 0.25% citric acid + 0.4% polyquaternium-37 | 4.3 |

[1]60 seconds at 25° C.

Examples 5-13

Example 5 was prepared by mixing 95% ethanol with water to form a 70% by weight ethanol mixture. Example 6 was prepared by dissolving urea in water to form a 10 wt. % mixture. Example 7 was prepared as for Example 5, except that urea was also added. Example 8 was prepared as for Example 7, except that polyquaternium-37 was also added. The pH of Example 8 was about 5.5. Example 9 was prepared as for Example 5, except that polyquaternium-22 was also added. Example 10 was prepared as for Example 9, except that urea was also added. The pH of Example 10 was about 4.9. Example 11 was prepared as for Example 5, except that guanidine HCl was also added. The pH of Example 11 was about 7.6. Example 12 was prepared as for Example 11, except that polyquaternium-22 was also added. The pH of Example 12 was about 6.2. Example 13 was prepared as for Example 12. The pH of Example 13 was about 5.8. The antiviral efficacy of Examples 5-13 were tested as described above for MS2, and the results are shown in Table 3.

TABLE 3

| EXAMPLE | COMPOSITION | LOG KILL, MS2[1] |
| --- | --- | --- |
| 5 | 70% ethanol | 0 |
| 6 | 10% urea in water | 0 |
| 7 | 70% ethanol + 10% urea | 0.9 |
| 8 | 70% ethanol + 10% urea + 0.4% polyquaternium-37 | ≧6.1 |
| 9 | 70% ethanol + 1% polyquaternium-22 | 0.7 |
| 10 | 70% ethanol + 10% urea + 0.4% polyquaternium-22 | 6.1 |
| 11 | 70% ethanol + 10% guanidine HCl | 2.7 |
| 12 | 70% ethanol + 10% guanidine HCl + 0.4% polyquaternium-22 | 5.5 |
| 13 | 70% ethanol + 10% aminoguanidine HCl + 0.4% polyquaternium-22 | 5.8 |

[1]60 seconds at 25° C.

Examples 14-15

Example 14 was prepared as described for Example 1, and Example 15 was prepared as described for Example 4. The efficacy of Examples 14 and 15 against feline calicivirus was tested by using a modification of the Standard Test Method for Efficacy of Virucidal Agents Intended for Special Applications (ASTM E1052). The samples were tested by in-vitro virucidal suspension assay. The F-9 strain of Feline Calicivirus stock virus was obtained from the American Type Culture Collection, Manassas, Va. (ATCC VR-782). A suspension of virus was exposed to the sample. At a pre-determined exposure time, an aliquot was removed, neutralized by serial dilution, and assayed for the presence of virus by infecting CRFK cells and measuring CPE as described hereinabove. Positive virus controls, cytotoxicity controls, and neutralization controls were assayed in parallel. Log reduction was calculated, and the results are shown in Table 4.

TABLE 4

| EXAMPLE | COMPOSITION | LOG KILL, FELINE CALICIVIRUS[1] |
| --- | --- | --- |
| 14 | 78% ethanol | 3.4 |
| 15 | 78% ethanol + 0.25% citric acid + 0.4% polyquaternium-37 | ≧4.7 |

[1]30 seconds at 33° C.

Examples 16-17

Example 16 was prepared as described for Example 2, and Example 17 was prepared as described for Example 4. The efficacy of Examples 16 and 17 against adenovirus type 2 was tested by using a modification of ASTM E1052. The samples were tested by in-vitro virucidal suspension assay. The Adenoid 6 strain of Adenovirus type 2 stock virus was obtained from the American Type Culture Collection, Manassas, Va. (ATCC VR-846). A suspension of virus was exposed to the sample. At a pre-determined exposure time, an aliquot was removed, neutralized by serial dilution, and assayed for the presence of virus. Positive virus controls, cytotoxicity controls, and neutralization controls were assayed in parallel. Log reduction was calculated, and the results are shown in Table 5.

TABLE 5

| EXAMPLE | COMPOSITION | LOG KILL, ADENOVIRUS[1] |
| --- | --- | --- |
| 16 | 78% ethanol + 0.25% citric acid | 1.3 |
| 17 | 78% ethanol + 0.25% citric acid + 0.4% polyquaternium-37 | ≧5.0 |

[1]30 seconds at 33° C.

Examples 18-20

Example 18 was prepared as described for Example 4, except that the concentration of ethanol was 70% by weight. Example 19 was prepared as described for Example 4. Example 20 was prepared as described for Example 4, except that tartaric acid was used instead of citric acid. The mixtures were tested for efficacy against five different viruses, and the results are shown in Table 6.

The efficacy of Examples 18-20 against rhinovirus type 37 was tested by using a modification of ASTM E1052. The samples were tested by in-vitro virucidal suspension assay. The 151-1 strain of Rhinovirus type 37 stock virus was obtained from the American Type Culture Collection, Manassas, Va. (ATCC VR-1147). A suspension of virus was exposed to the sample. At a pre-determined exposure time, an aliquot was removed, neutralized by serial dilution, and assayed for the presence of virus by infecting MRC-5 cells and measuring CPE as described hereinabove. Positive virus controls, cytotoxicity controls, and neutralization controls were assayed in parallel.

The efficacy of Examples 18-20 against rotovirus was tested by using a modification of ASTM E1052. The samples were tested by in-vitro virucidal suspension assay. The WA stock virus was obtained from the American Type Culture Collection, Manassas, Va. (ATCC VR-2018). A suspension of virus was exposed to the sample. At a pre-determined exposure time, an aliquot was removed, neutralized by serial dilution, and assayed for the presence of virus by infecting MA-104 cells and measuring CPE as described hereinabove. Positive virus controls, cytotoxicity controls, and neutralization controls were assayed in parallel.

TABLE 6

| EX. | COMPOSITION | MS2[1] | FELINE CALICIVIRUS[2] | ADENOVIRUS[3] | ROTAVIRUS[4] | RHINOVIRUS[5] |
|---|---|---|---|---|---|---|
| 18 | 70% ethanol + 0.25% citric acid + 0.4% polyquaternium-37 | 2.4 | ≧4.7 | ≧5.0 | ≧3.8 | ≧3.3 |
| 19 | 78% ethanol + 0.25% citric acid + 0.4% polyquaternium-37 | 3.7 | ≧4.7 | ≧5.0 | ≧3.8 | ≧3.3 |
| 20 | 78% ethanol + 0.25% tartaric acid + 0.4% polyquaternium-37 | 4.4 | ≧4.7 | ≧5.0 | ≧3.8 | ≧3.3 |

[1]60 seconds at 25° C.; average of replicates;
[2-5]30 seconds at 33° C.

Examples 21-22

Example 21 was prepared by mixing 95% ethanol with water to form a 78% by weight ethanol mixture. Example 22 was prepared as for Example 21, except that polyquaternium-37 was also added. The efficacy of Examples 21-22 against hepatitis A virus was tested by using a modification of ASTM E1052. The samples were tested by in-vitro virucidal suspension assay. The HM-175 strain of Hepatities A virus (HAV) stock virus was obtained from AppTec Laboratory Services, Camden, N.J. A suspension of virus was exposed to the sample. At a pre-determined exposure time, an aliquot was removed, neutralized by serial dilution, and assayed for the presence of virus by infecting FRhK-4 cells and measuring CPE as described hereinabove. Positive virus controls, cytotoxicity controls, and neutralization controls were assayed in parallel. Results are shown in Table 7.

TABLE 7

| EXAMPLE | COMPOSITION | LOG KILL, HEPATITIS A VIRUS[1] |
|---|---|---|
| 21 | 78% ethanol | 1.25 |
| 22 | 78% ethanol + 1% polyquaternium-37 | 3.0 |

[1]60 seconds at 25° C.

Examples 23-24

Example 23 was prepared as for Example 18. Example 24 represents an antibacterial hand sanitizer composition similar to a product currently commercially available, the label of which is marked with U.S. Pat. No. 6,080,417. The efficacy of Examples 23-24 against Canine parvovirus was tested by using a modification of ASTM E1052. The samples were tested by in-vitro virucidal suspension assay. The virus tested was Strain Cornell, ATCC VR-2017, cell line A-72 canine tumor cells, ATCC CRL-1542. A suspension of virus was exposed to the sample. At a pre-determined exposure time, an aliquot was removed, neutralized by serial dilution, and assayed for the presence of virus by infecting CRFK cells and measuring CPE as described hereinabove. Positive virus controls, cytotoxicity controls, and neutralization controls were assayed in parallel. Results are shown in Table 8.

TABLE 8

| EXAMPLE | COMPOSITION | LOG KILL, CANINE PARVOVIRUS |
|---|---|---|
| 23 | 70% ethanol + 0.25% citric acid + 0.4% polyquaternium-37 | 1.0 |
| 24 | Manorapid Synergy | 0 |

30 seconds at 33° C.

Examples 25-26

Examples 25-26 represent antibacterial hand sanitizer compositions similar to products currently commercially available. The compositions were formulated as shown in Table 9, and tested for efficacy against MS2.

TABLE 9

| EXAMPLE | COMPOSITION | LOG KILL, MS2[1] |
|---|---|---|
| 25 | 62% ethanol in carbomer gel | 0 |
| 26 | Manorapid Synergy | 0.8 |

[1] 60 seconds at 25° C.

Fingerpad in vivo testing of Examples 19 and 23 was performed according to ASTM E 1838-96, "Standard Test Method for Determining the Virus-Eliminating Effectiveness of Liquid Hygienic Handwash Agents Using the Fingerpads of Adult Volunteers." The efficacy of the compositions was tested against feline calicivirus and rotovirus, and the results are shown in Table 10.

TABLE 10

| EXAMPLE | COMPOSITION | LOG KILL, FELINE CALICIVIRUS[1] | LOG KILL, ROTAVIRUS[1] |
|---|---|---|---|
| Example 23 | 62% ethanol in carbomer gel | 0.6 | 2.5 |
| Example 19 | 78% ethanol + 0.25% citric acid + 0.4% polyquaternium-37 | 1.6 | 3.0 |

[1] $\log_{10}$ reduction at 15 seconds

Examples 25-26

The efficacy of Examples 25-26 against herpes virus (an enveloped virus) was tested by in-vitro virucidal suspension assay. (Herpes Simplex Type 1 Strain F(1), ATCC VR-733 grown on rabbit kidney cells (RK) from ViroMed Laboratories) A suspension of virus was exposed to the sample. At a pre-determined exposure time, an aliquot was removed, neutralized by serial dilution, and assayed for the presence of virus by infecting RK cells and measuring CPE as described hereinabove. Positive virus controls, cytotoxicity controls, and neutralization controls were assayed in parallel. Results are shown in Table 11.

TABLE 11

| EXAMPLE | COMPOSITION | LOG KILL HERPES VIRUS[1] |
|---|---|---|
| 25 | 62% ethanol in carbomer gel | ≧5.5 |
| 26 | 62% ethanol + 1.5% polyquaternium-37 | ≧4.5 |

[1] 60 seconds at room temperature

Thus, it should be evident that the present invention provides a method for inactivating virus. In certain embodiments, a virucidal composition comprising alcohol, a cationic oligomer or polymer, and an enhancer exhibits an efficacy against non-enveloped viruses that is higher than the efficacy of the same composition but not comprising the enhancer. In one embodiment, the virucidal composition exhibits an efficacy against non-enveloped viruses that is at least about 0.5 log kill higher than the efficacy of the same composition but not comprising the enhancer. In another embodiment, the composition exhibits an efficacy against non-enveloped viruses that is at least about 1 log kill higher than the efficacy of the same composition but not comprising the enhancer.

The antiviral composition is highly efficacious for household cleaning applications (e.g., hard surfaces like floors, countertops, tubs, dishes and softer cloth materials like clothing, sponges, paper towels, etc.), personal care applications (e.g. lotions, shower gels, soaps, hand sanitizers, shampoos, wipes) and industrial and hospital applications (e.g., disinfection of instruments, surfaces, medical devices, gloves). This composition is efficacious for rapidly sanitizing or de-germing surfaces that are infected or contaminated with Gram negative bacteria, fungi, parasites, Gram positive bacteria, enveloped viruses, and non-enveloped viruses. The efficacy of alcoholic compositions comprising a C1-6 alcohol, an acid, and a cationic oligomer or polymer against resident and transient flora is described in co-pending U.S. Provisional Patent Application Ser. No. 60/771,784, which is hereby incorporated by reference in its entirety.

Various modifications and alterations that do not depart from the scope and spirit of this invention will become apparent to those skilled in the art. This invention is not to be duly limited to the illustrative embodiments set forth herein.

What is claimed is:

1. A method of inactivating non-enveloped virus particles, the method comprising:
   contacting non-enveloped virus particles under conditions suitable to inactivate non-enveloped virus particle with a virucidally-enhanced alcoholic composition comprising:
   a. at least 50 percent by weight of a $C_{1-6}$ alcohol, based upon the total weight of the alcoholic composition; and
   b. an enhancer selected from the group consisting of at least 0.01 percent by weight, based upon the total weight of the alcoholic composition of at least one proton donor, from about 0.25 to about 20 percent by weight, based upon the total weight of the alcoholic composition of at least one chaotropic agent, and mixtures thereof, with the proviso that when the alcoholic composition comprises a proton donor, the composition further comprises a synergistic amount of a cationic oligomer or polymer; thereby
   inactivating non-enveloped virus particles, wherein said method exhibits at least a 1 log reduction against said non-enveloped virus particles in 60 seconds or less, compared to contacting said particles with a composition containing the same amount of C1-6 alcohol without said enhancer for the same amount of time.

2. The method of claim 1, wherein said method is operative to inactivate enveloped virus particles and wherein said method further comprises:
   contacting the enveloped virus particles with said composition.

3. The method of claim 1, wherein said method is operative to kill microbes including gram positive bacteria, gram negative bacteria, fungi and parasites, and wherein said method further comprises:
   contacting microbes with said composition.

4. The method of claim 1, wherein said composition comprises from 50 to about 98 percent by weight of a $C_{1-6}$ alcohol, from 0.01 to about 1 percent by weight of a proton donor, and from about 0.02 to about 20 percent by weight of a cationic oligomer or polymer, all based upon the total weight of the alcoholic composition.

5. The method of claim 4, wherein said cationic oligomer or polymer is a cationic polysaccharide, cationic copolymer of saccharide and a synthetic cationic monomer, cationic polyalkylene imine, cationic ethoxy polyalkylene imine, cationic poly [N-[3-(dialkylammonio)alkyl] N'[3-(alkyleneoxy-alkylene dialkylammonio) alkyl]urea dichloride], vinyl caprolactam/VP/dialkylaminoalkyl alkylate copolymer, polyquaternium polymer or mixtures thereof.

6. The method of claim 5, wherein said cationic oligomer or polymer is polyquaternium-2, polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-32, polyquaternium-37, polyquaternium-39, polyquaternium-42, polyquaternium-43, polyquaternium-44, polyquaternium-46, polyquaternium-47, polyquaternium-51, polyquaternium-53, polyquaternium-55, polyquaternium-57, polyquaternium-58, polyquaternium-59, polyquaternium-60, polyquaternium-63, polyquaternium-64, polyquaternium-65, polyquaternium-68, or mixtures thereof.

7. The method of claim 4, wherein said cationic oligomer or polymer is characterized by a charge density of at least about 0.1 meq/g.

8. The method of claim 1, wherein said composition comprises from about 60 to about 95 percent by weight of a $C_{1-6}$ alcohol, a cationic oligomer or polymer, and a proton donor.

9. The method of claim 8, wherein said composition comprises from about 0.015 to about 1 percent by weight of a proton donor, based upon the total weight of the alcoholic composition.

10. The method of claim 8, wherein said proton donor is hydrochloric acid, nitric acid, phosphoric acid, phosphonic acid, boric acid, sulfuric acid, adipic acid, benzene 1,3,5 tricarboxylic acid, chlorosuccinic acid, choline chloride, cis-aconitic acid, citramalic acid, citric acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, lactic acid, maleic acid, malic acid, malonic acid, nitrilotriacetic acid, oxalacetic acid, oxalic acid, phytic acid, p-toluenesulfonic acid, salicylic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxo-glutaric acid, dl-glyceric acid, 2,5 furandicarboxylic acid, or mixtures thereof.

11. The method of claim 1, wherein said composition comprises a $C_{1-6}$ alcohol, a cationic oligomer or polymer, and a chaotropic agent.

12. The method of claim 1, wherein said composition comprises from about 0.25 to about 20 percent by weight chaotropic agent, based upon the total weight of the alcoholic composition.

13. The method of claim 1, wherein said chaotropic agent comprises thiourea, guanidine HCl, guanidine thiocyanate, aminoguanidine HCl, aminoguanidine bicarbonate, guanidine carbonate, guanidine phosphate, or mixtures thereof.

14. The method of claim 1, wherein said method exhibits at least a 2 log reduction against said non-enveloped virus particles in 60 seconds or less.

15. The method of claim 1, wherein said method exhibits at least a 3 log reduction against said non-enveloped virus particles in 60 seconds or less.

16. The method of claim 1, wherein said non-enveloped virus particles are selected from members of the families Picornaviridae, Reoviridae, Caliciviridae, Adenoviridae and Parvoviridae.

17. The method of claim 1, wherein said non-enveloped virus particles are selected from adenovirus, feline calicivirus, norovirus, papillomavirus, poliovirus, rhinovirus, hepatitis A virus, parvovirus, and rotavirus.

18. A method of producing a topical virucidal effect on mammalian skin against non-enveloped virus particles by applying a virucidally-enhanced alcoholic composition said method comprising topically applying to mammalian skin a virucidally-enhanced composition comprising:
  a. at least 50 percent by weight of a $C_{1-6}$ alcohol, based upon the total weight of the alcoholic composition; and
  b. an enhancer selected from the group consisting of at least 0.01 percent by weight, based upon the total weight of the alcoholic composition of at least one proton donor, from about 0.25 to about 20 percent by weight, based upon the total weight of the alcoholic composition of at least one chaotropic agent, and mixtures thereof, with the proviso that when the alcoholic composition comprises a proton donor, the composition further comprises a synergistic amount of a cationic oligomer or polymer; thereby producing a virucidal effect against non-enveloped virus particles on said skin, wherein said method exhibits at least a 1 log reduction against said non-enveloped virus particles in 60 seconds or less.

19. The method of claim 18, wherein said method further produces a topical virucidal effect against enveloped viruses.

20. The method of claim 18, wherein said method further produces a topical virucidal effect against microbes including gram positive bacteria, gram negative bacteria, fungi, parasites.

21. The method of claim 18, wherein said composition comprises at least about 60 percent by weight of a $C_{1-6}$ alcohol, based upon the total weight of the alcoholic composition.

22. The method of claim 18, wherein said composition comprises from 50 to about 98 percent by weight of a $C_{1-6}$ alcohol, from 0.01 to about 1 percent by weight of a proton donor, and from about 0.02 to about 20 percent by weight of a cationic oligomer or polymer, all based upon the total weight of the alcoholic composition.

23. The method of claim 22, wherein said cationic oligomer or polymer is a cationic polysaccharide, cationic copolymer of saccharide and a synthetic cationic monomer, cationic polyalkylene imine, cationic ethoxy polyalkylene imine, cationic poly [N- [3-(dialkylammonio)alkyl] N' [3-(alkyleneoxyalkylene dialkylammonio)alkyl]urea dichloride], vinyl caprolactam/VP/dialkylaminoalkyl alkylate copolymer, polyquaternium polymer or mixtures thereof.

24. The method of claim 22, wherein said cationic oligomer or polymer is polyquaternium-2, polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-32, polyquaternium-37, polyquaternium-39, polyquaternium-42, polyquaternium-43, polyquaternium-44, polyquaternium-46, polyquaternium-47, polyquaternium-51, polyquaternium-53, polyquaternium-55, polyquaternium-57, polyquaternium-58, polyquaternium-59, polyquaternium-60, polyquaternium-63, polyquaternium-64, polyquaternium-65, polyquaternium-68, or mixtures thereof.

25. The method of claim 22, wherein said cationic oligomer or polymer is characterized by a charge density of at least about 0.1 meq/g.

26. The method of claim 18, wherein said composition comprises from about 60 to about 95 percent by weight of a $C_{1-6}$ alcohol, a cationic oligomer or polymer, and a proton donor.

27. The method of claim 26, wherein said composition comprises from about 0.015 to about 1 percent by weight of a proton donor, based upon the total weight of the alcoholic composition.

28. The method of claim 18, wherein said proton donor is hydrochloric acid, nitric acid, phosphoric acid, phosphonic acid, boric acid, sulfuric acid, adipic acid, benzene 1,3,5 tricarboxylic acid, chlorosuccinic acid, choline chloride, cis-aconitic acid, citramalic acid, citric acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, lactic acid, maleic acid, malic acid, malonic acid, nitrilotriacetic acid, oxalacetic acid, oxalic acid, phytic acid, p-toluenesulfonic acid, salicylic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxo-glutaric acid, dl-glyceric acid, 2,5 furandicarboxylic acid, or mixtures thereof.

29. The method of claim 18, wherein said composition comprises $C_{1-6}$ alcohol, a cationic oligomer or polymer, and a chaotropic agent.

30. The method of claim 29, wherein said composition comprises from about 0.25 to about 20 percent by weight chaotropic agent, based upon the total weight of the alcoholic composition.

31. The method of claim 29, wherein said chaotropic agent is thiourea, guanidine HCl, guanidine thiocyanate, aminoguanidine HCl, aminoguanidine bicarbonate, guanidine carbonate, guanidine phosphate, or mixtures thereof.

32. The method of claim 18, wherein said method exhibits at least a 2 log reduction against said non-enveloped virus particles in 60 seconds or less.

33. The method of claim 18, wherein said method exhibits at least a 3 log reduction against said non-enveloped virus particles in 60 seconds or less.

34. The method of claim 18, wherein said non-enveloped virus particles are selected from members of the families Picornaviridae, Reoviridae, Caliciviridae, Adenoviridae and Parvoviridae.

35. The method of claim 18, wherein said non-enveloped virus particles are selected from adenovirus, feline calicivirus, norovirus, papillomavirus, poliovirus, rhinovirus, hepatitis A virus, parvovirus, and rotavirus.

36. A method of enhancing the efficacy of a $C_{1-6}$ alcohol against non-enveloped virus particles in a topical application to a surface, the method comprising:
combining said $C_{1-6}$ alcohol with an efficacy-enhancing amount of an enhancer selected from the group consisting of proton donors, chaotropic agents, and mixtures thereof, to form an antiviral composition that comprises at least 50 percent by weight of said $C_{1-6}$ alcohol, based upon the total weight of the composition, with the proviso that where the antiviral composition comprises a proton donor, the composition further comprises a synergistic amount of a cationic oligomer or polymer, wherein said antiviral composition exhibits an increased efficacy against non-enveloped viruses when applied to a surface for 60 seconds or less, compared to a composition containing the same amount of $C_{1-6}$ alcohol without said enhancer that is applied to a surface for the same amount of time.

37. The method of claim 36, wherein said method further produces a topical virucidal effect against enveloped viruses.

38. The method of claim 36, wherein said method further produces a topical virucidal effect against microbes including gram positive bacteria, gram negative bacteria, fungi, parasites.

39. The method of claim 36, wherein said composition comprises at least about 60 percent by weight of a $C_{1-6}$ alcohol, based upon the total weight of the antiviral composition.

40. The method of claim 36, wherein said composition comprises from about 50 to about 98 percent by weight of a $C_{1-6}$ alcohol, from about 0.01 to about 1 percent by weight of a proton donor, and from about 0.02 to about 20 percent by weight of a cationic oligomer or polymer, all based upon the total weight of the alcoholic composition.

41. The method of claim 40, wherein said cationic oligomer or polymer is a cationic polysaccharide, cationic copolymer of saccharide and a synthetic cationic monomer, cationic polyalkylene imine, cationic ethoxy polyalkylene imine, cationic poly [N-[3-(dialkylammonio)alkyl] N'[3-(alkyleneoxyalkylene dialkylammonio)alkyl]urea dichloride], vinyl caprolactam/VP/dialkylaminoalkyl alkylate copolymer, polyquaternium polymer or mixtures thereof.

42. The method of claim 40, wherein said cationic oligomer or polymer includes polyquaternium-2, polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-32, polyquaternium-37, polyquaternium-39, polyquaternium-42, polyquaternium-43, polyquaternium-44, polyquaternium-46, polyquaternium-47, polyquaternium-51, polyquaternium-53, polyquaternium-55, polyquaternium-57, polyquaternium-58, polyquaternium-59, polyquaternium-60, polyquaternium-63, polyquaternium-64, polyquaternium-65, polyquaternium-68, or mixtures thereof.

43. The method of claim 40, wherein said cationic oligomer or polymer is characterized by a charge density of at least about 0.1 meq/g.

44. The method of claim 36, wherein said composition comprises a $C_{1-6}$ alcohol, a cationic oligomer or polymer, and a proton donor.

45. The method of claim 44, wherein said composition comprises from about 0.015 to about 1 percent by weight of a proton donor, based upon the total weight of the alcoholic composition.

46. The method of claim 44, wherein said proton donor is hydrochloric acid, nitric acid, phosphoric acid, phosphonic acid, boric acid, sulfuric acid, adipic acid, benzene 1,3,5 tricarboxylic acid, chlorosuccinic acid, choline chloride, cis-aconitic acid, citramalic acid, citric acid, cyclobutane 1,1,3,3 tetracarboxylic acid, cyclohexane 1,2,4,5 tetracarboxylic acid, cyclopentane 1,2,3,4 tetracarboxylic acid, diglycolic acid, fumaric acid, glutamic acid, glutaric acid, glyoxylic acid, isocitric acid, ketomalonic acid, lactic acid, maleic acid, malic acid, malonic acid, nitrilotriacetic acid, oxalacetic acid, oxalic acid, phytic acid, p-toluenesulfonic acid, salicylic acid, succinic acid, tartaric acid, tartronic acid, tetrahydrofuran 2,3,4,5 tetracarboxylic acid, tricarballylic acid, versene acids, 3-hydroxyglutaric acid, 2-hydroxypropane 1,3 dicarboxylic acid, glyceric acid, furan 2,5 dicarboxylic acid, 3,4-dihydroxyfuran-2,5 dicarboxylic acid, 3,4-dihydroxytetrahydrofuran-2,5-dicarboxylic acid, 2-oxo-glutaric acid, dl-glyceric acid, 2,5 furandicarboxylic acid, or mixtures thereof.

47. The method of claim 36, wherein said composition comprises $C_{1-6}$ alcohol, a cationic oligomer or polymer, and a chaotropic agent.

48. The method of claim 36, wherein said composition comprises from about 0.25 to about 20 percent by weight chaotropic agent, based upon the total weight of the antiviral composition.

49. The method of claim 36, wherein said chaotropic agent is urea, thiourea, guanidine HCl, guanidine thiocyanate, aminoguanidine HCl, aminoguanidine bicarbonate, guanidine carbonate, guanidine phosphate, or mixtures thereof.

50. The method of claim 36, wherein said method exhibits at least a 1 log reduction against said non-enveloped virus particles in 60 seconds or less.

51. The method of claim 36, wherein said method exhibits at least a 3 log reduction against said non-enveloped virus particles in 60 seconds or less.

52. The method of claim 36, wherein said surface includes a porous or non-porous surface.

53. The method of claim 36, wherein said non-enveloped virus particles are selected from members of the families Picornaviridae, Reoviridae, Caliciviridae, Adenoviridae and Parvoviridae.

54. The method of claim 36, wherein said non-enveloped virus particles are selected from adenovirus, feline calicivirus, norovirus, papillomavirus, poliovirus, rhinovirus, hepatitis A virus, parvovirus, and rotavirus.

* * * * *